(12) United States Patent
Gibson et al.

(10) Patent No.: US 6,951,847 B2
(45) Date of Patent: Oct. 4, 2005

(54) METHODS OF TREATING FUNGAL INFECTIONS USING LUPEOL

(75) Inventors: David J. Gibson, Woodbury, NJ (US); Robert M. Carlson, Duluth, MN (US)

(73) Assignees: Regents of the University of Minnesota, Minneapolis, MN (US); NaturNorth Technologies, LLC, Duluth, MN (US)

( * ) Notice: Subject to any disclaimer, the term of this patent is extended or adjusted under 35 U.S.C. 154(b) by 0 days.

(21) Appl. No.: 10/431,351

(22) Filed: May 7, 2003

(65) Prior Publication Data

US 2004/0072807 A1 Apr. 15, 2004

Related U.S. Application Data

(63) Continuation-in-part of application No. 09/969,553, filed on Oct. 1, 2001, now Pat. No. 6,642,217.
(60) Provisional application No. 60/237,756, filed on Sep. 29, 2000.

(51) Int. Cl.[7] .................... A61K 31/56; A01N 25/00; C07J 53/00
(52) U.S. Cl. .................... 514/169; 514/171; 514/182; 514/844; 552/510
(58) Field of Search .................... 514/169, 171, 514/844, 182; 552/510

(56) References Cited

U.S. PATENT DOCUMENTS

| | | | |
|---|---|---|---|
| 4,559,157 A | 12/1985 | Smith et al. | 252/90 |
| 4,608,392 A | 8/1986 | Jacquet et al. | 514/844 |
| 4,820,508 A | 4/1989 | Wortzman | 424/59 |
| 4,938,949 A | 7/1990 | Borch et al. | 424/10 |
| 4,992,478 A | 2/1991 | Geria | 514/782 |
| 6,303,589 B1 * | 10/2001 | Glinski et al. | 514/169 |
| 6,642,217 B2 * | 11/2003 | Krasutsky et al. | 514/169 |

FOREIGN PATENT DOCUMENTS

JP  05-186326  *  7/1993

* cited by examiner

Primary Examiner—Paul A. Zucker
(74) Attorney, Agent, or Firm—Schwegman, Lundberg, Woessner & Kluth, P.A.

(57) ABSTRACT

The invention is directed to methods of treating fungal and yeast infections using lupeol or solvates, hydrates, or clathrates thereof. The method also encompasses methods of treating fungal and yeast infections by administering to a mammal in need of such treatment a therapeutically effective amount of lupeol. Among the methods used include topical formulations for the improvement of skin appearance.

24 Claims, 1 Drawing Sheet

Antifungal Activity Against *Trichophyton Mentagrophytes*

Lupeol, Lupeol Derivative, and 3-Substituted Lupeol Derivative Samples and Controls Lupeol, Lupeol Derivative, and 3-Substituted Lupeol Derivative Samples and Controls

METHODS OF TREATING FUNGAL INFECTIONS USING LUPEOL

PRIORITY OF INVENTION

This application is a continuation-in-part application of U.S. application Ser. No. 09/969,553, filed on Oct. 1, 2001, now U.S. Pat. No. 6,642,217, which claims the benefit of U.S. provisional application No. 60/237,756, filed on Sep. 29, 2000.

BACKGROUND OF THE INVENTION

Lupeol is a pentacyclic triterpenoid derived from the outer bark of paper birch trees (*Betula paperifera*). Lupeol is present at concentrations of about 1.5–3% of birch bark and at up to about 8.2% in *Canavalia ensiformis*, a plant widespread in the humid tropics of Asia, India, and Africa. A typical pulp mill that processes birch produces enough bark waste to allow for the inexpensive isolation of significant quantities of Lupeol.

Fungi infect humans and are a major cause of human health problems. They also infect plants and cause enormous losses in agricultural productivity. One class of fungal infections of mammals are the dermatophytic infections. These are fungal infections of the hair, nails, and skin. They are caused by fungi called "dermatophytes," which include species belonging to the genera *Epidermophyton, Microsporum*, and *Trichophyton*. Among the species of dermatophytes are the following: *Microsporum canis*, which results in scalp and skin infections, mostly in children; *Microsporum gypseum*, which also results in scalp and skin infections in animals and humans; *Trichophyton tonsurans*, the major agent causing scalp ringworm; *Trichophyton rubrum*, causing skin, nail, hair, and scalp infections; and *Trichophyton mentagrophytes*, which can occur on all parts of the body surface.

Other fungal infectious agents include the opportunists that are likely to infect immunodeficient persons. These include *Cryptococcus, Candida*, and *Aspergillus*.

Current agents used to treat fungal infections include the polyene antibiotics, including nystatin; synthetic azoles; and griseofulvin. Fungal infections are difficult to treat because, like humans, they are eukaryotes.

Currently, there is a need for new anti-fungal and anti-yeast agents. A need particularly exists for agents that will act against a range of species, including dermatophytic fungi, yeasts, and *Candida*. New anti-fungal agents would be less expensive to manufacture if they were abundant natural products or easily synthesized from abundant natural products.

SUMMARY OF THE INVENTION

The present invention provides a method for treating a fungal infection or yeast infection in a mammal. The method includes administering to the mammal in need of such treatment or at risk thereof a therapeutically effective amount of lupeol.

The present invention also provides a method for enhancing skin appearance in a mammal (e.g., human). The method includes administering to the skin of the mammal in need of such appearance enhancement or at risk thereof, a topical composition that includes a cosmetically effective amount of lupeol.

The present invention also provides a pharmaceutical composition that includes a pharmaceutically acceptable carrier and a therapeutically effective amount of lupeol.

The present invention also provides a cosmetic composition that includes a cosmetically or pharmaceutically acceptable carrier and a cosmetically effective amount of lupeol. The cosmetic composition is useful, e.g., for skin care and for enhancing skin appearance.

DETAILED DESCRIPTION

Figure 1:
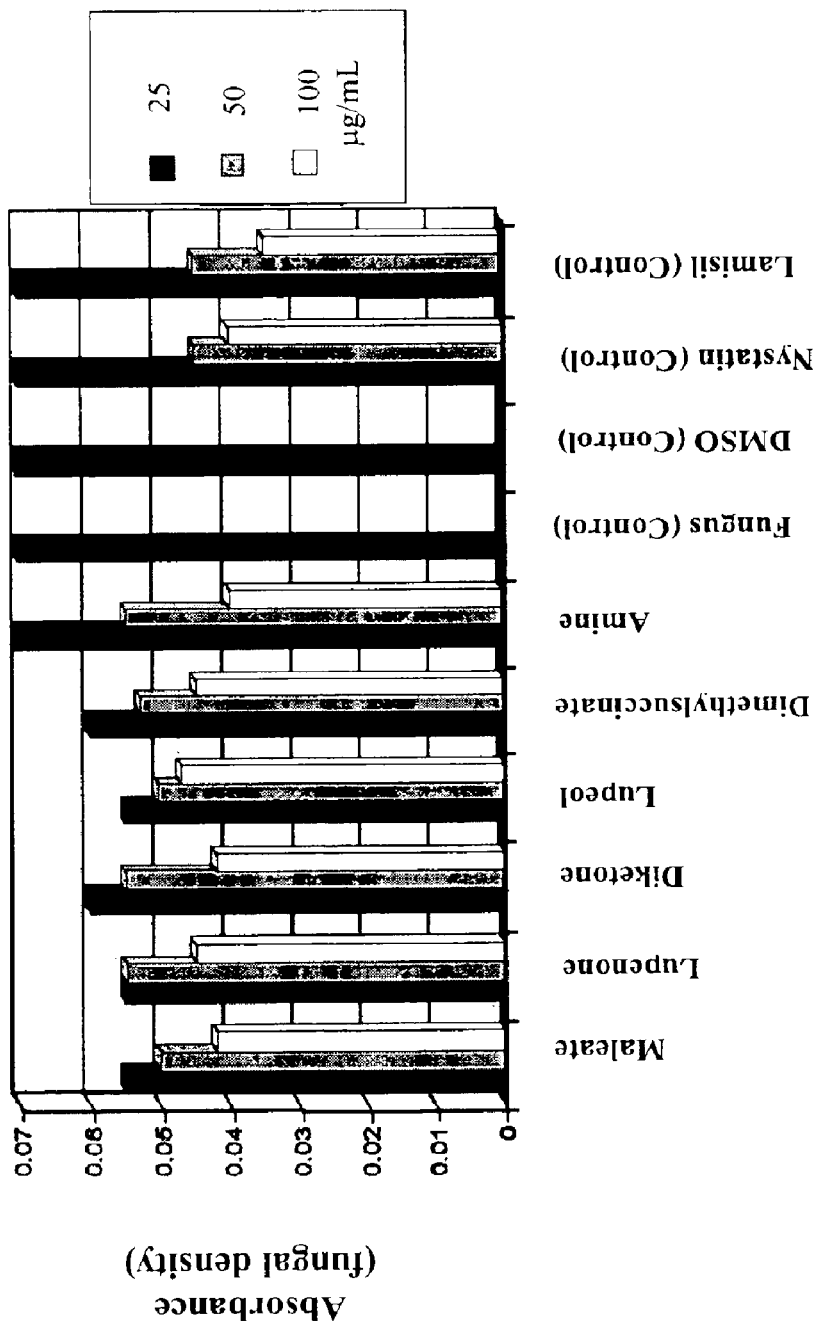
FIG. 1 is a graphical depiction of the results of growth inhibition studies on *Trichophyton mentagrophytes* in liquid culture with lupeol, lupeol derivatives, and lupeol derivatives substituted at the 3-position.

The term "fungus" refers to a distinct group of eukaryotic, spore-forming organisms wih absorptive nutrition and lacking chlorophyll. It includes mushrooms, molds, and yeasts. One class of fungal infections of mammals are the dermatophytic infections. These are fungal infections of the hair, nails, and skin. They are caused by fungi called "dermatophytes," which include species belonging to the genera *Epidermophyton, Microsporum*, and *Trichophyton*. Among the species of dermatophytes are the following: *Microsporum canis*, which results in scalp and skin infections, mostly in children; *Microsporum gypseum*, which also results in scalp and skin infections in animals and humans; *Trichophyton tonsurans*, the major agent causing scalp ringworm; *Trichophyton rubrum*, causing skin, nail, hair, and scalp infections; and *Trichophyton mentagrophytes*, which can occur on all parts of the body surface. Other fungal infectious agents include the opportunists that are likely to infect immunodeficient persons. These include *Cryptococcus, Candida*, and *Aspergillus*.

The structure and carbon numbering of Lupeol is shown below.

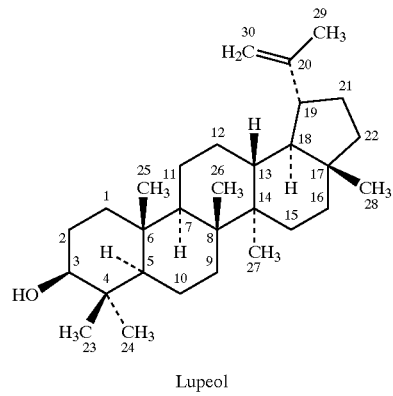

Lupeol

As used herein, "lupeol" includes all metabolites, prodrugs, solvates, hydrates, and clathrates thereof.

The lupeol can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the lupeol may be systemically administered, e.g., orally, in combination with a pharmaceutically acceptable vehicle such as an inert diluent or an assimilable edible carrier. The lupeol may be enclosed in hard or soft shell gelatin capsules, may be compressed into tablets, or may be incorporated directly with the food of the patient's diet. For oral therapeutic administration, the lupeol may be combined with one or more excipients and used in the form of ingestible tablets, buccal tablets, troches, capsules, elixirs, suspensions, syrups, wafers, and the like. Such compositions and preparations should contain at least 0.1% of lupeol. The percentage of the compositions and preparations may, of course, be varied and may conveniently be between about 2 to about 60% of the weight of a given unit dosage form. The amount of lupeol in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the lupeol, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the lupeol may be incorporated into sustained-release preparations and devices.

The lupeol may also be administered intravenously or intraperitoneally by infusion or injection. Solutions of the lupeol can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the lupeol which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the lupeol in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the lupeol plus any additional desired ingredient present in the previously sterile-filtered solutions.

For topical administration, the lupeol may be applied in pure form. However, it will generally be desirable to administer lupeol to the skin as a composition or formulation, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the lupeol can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the lupeol to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the lupeol can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the lupeol in a liquid composition, such as a lotion, will be from about 0.1–25 wt-%, preferably from about 0.5–10 wt-%. The concentration in a semisolid or solid composition such as a gel or a powder will be about 0.1–5 wt-%, preferably about 0.5–2.5 wt-%.

The amount of the lupeol required for use in treatment will vary not only with the route of administration, but with the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The lupeol is conveniently administered in unit dosage form; for example, containing 5 to 1000 mg, conveniently 10 to 750 mg, most conveniently, 50 to 500 mg of lupeol per unit dosage form.

Ideally, the lupeol should be administered to achieve peak plasma concentrations of the lupeol of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the lupeol, optionally in saline, or orally administered as a bolus containing about 1–100 mg of the lupeol. Desirable blood levels may be maintained by continuous infusion to provide about 0.01–5.0 mg/kg/hr or by intermittent infusions containing about 0.4–15 mg/kg of the lupeol.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of lupeol to act as an anti-fungal or anti-yeast agent may be determined using pharmacological models which are well known to the art, including the tests described in the Examples below.

The lupeol may be also be useful as pharmacological tools for the further investigation of the mechanism of their anti-fungal action.

The lupeol can also be administered in combination with other therapeutic agents that are effective to treat fungal or yeast infections, or to inhibit or kill a fungus or yeast. The methods of the invention may further encompass the administration of lupeol in combination with at least one other therapeutic agent, effective to inhibit or kill fungal or yeast infections. The therapeutic agents include, but are not limited to, antiviral, antifungal, or antibiotic agents, and are known to the those skilled in the art. Examples of other antifungal agents include, but are not limited to, allylamine antifungal agents, such as terbinafine HCl and naftifine HCl; amphotericin B; benzylamine antifungal agents such as butenafine HCl; chloroxylenol; ciclopirox; flucytosine; glucan synthesis inhibitors, such as caspofungin acetate; griseofulvin; triazole antifungal agents, such as clotrimazole, fluconazole, itraconazole, ketoconazole, miconazole nitrate, and oxiconazole nitrate; nystatin; and undecylenic acid. See, Physicians Desk Reference, Medical Economics Company, Inc. (2002). Other antifungal or anti-yeast agents include those in U.S. patent application Ser. No. 09/969,553 filed on Oct. 1, 2001, which is incorporated herein by reference.

The administration of lupeol with other therapeutic agents may be performed simultaneously or sequentially. The simultaneous administration refers to the administration of lupeol which has been combined with at least one other therapeutic agent prior to the administration to the patient in need of treatment for fungal or yeast infection of the mixture of therapeutic agents. The sequential administration refers to the administration of lupeol prior to administration of other therapeutic agents or vice versa.

The methods of the invention may be carried out in vivo or in vitro. The method of the invention encompasses inhibiting or killing a fungus or yeast by contacting the fungus or yeast with an effective anti-fungal or anti-yeast amount of lupeol in vitro or alternatively, in vivo.

External fungal infections, such as athletes foot and onychomycosis (fungal infections of the nails), exhibit visible skin or nail discoloration, lesions, neoplasms, or a combination thereof. In some cases of fungal infections, there may be a papule, a fixed subcutaneous nodule, a vesicle with an indurated base, or a subcutaneous abscess that ruptures to form a fistula to the skin surface. In other cases, the fungal infections exhibit small, itchy enlarging papules that may resemble dermatophytosis which later extend to form dull red or violaceous, sharply demarcated patches with indurated bases. Hard, dull red or grayish cauliflower-shaped nodular projections may develop in the center of the patches, gradually extending to cover the extremities.

The compositions used in the methods of the invention can be used to reduce, treat, or remove the exterior blemishes caused by fungal or yeast infections. In particular, the compositions can be used to improve the exterior skin appearance and remove physical signs associated with fungal or yeast infections. As used herein, the term "improve skin appearance" refers to removal or diminishment in appearance or size of skin or nail discolorations and skin blemishes associated with fungal or yeast infections. As used herein, the term "cosmetically effective amount" refers to an amount of lupeol or pharmaceutically acceptable salt thereof sufficient to improve skin appearance. As used herein, the term "treat" refers to eliminating or reducing the severity of a symptom associated with a fungal or yeast infection such as those described in The Merck Manual, $17^{th}$ ed. Merck Research Laboratories (1999). Pharmaceutical compositions for use in the methods of the present invention suitable for topical administration may be presented as discrete units including aerosol sprays, each containing a predetermined amount of the active ingredient, as a powder, stick, or granules, as creams (e.g., a conditioner), pastes, gels, lotions (e.g., a sunscreen), syrups, or ointments, on sponges or cotton applicators, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier(s) with the active ingredient, which constitutes one or more necessary ingredients. In general, the compositions are prepared by uniformly and intimately admixing the active ingredient with liquid carriers or finely divided solid carriers or both, and then, if necessary, shaping the product into the desired presentation.

Processes for preparing (i.e., manufacturing or isolating) lupeol can be found in U.S. patent application Ser. No. 09/969,553 filed on Oct. 1, 2001, which is incorporated herein to the extent necessary to enable the present invention. Additional methods of preparing lupeol are described in the examples below.

The enumerated embodiments below are non-limiting aspects of the present invention, and can be practiced as described herein:

[1] One embodiment of the present invention provides a method for treating a fungal infection or yeast infection in a mammal, the method comprising administering to the mammal in need of such treatment or at risk thereof a therapeutically effective amount of lupeol.

[2] Another embodiment of the present invention provides the method according to embodiment [1], wherein the fungal infection or yeast infection is caused by at least one dermatophytic fungus.

[3] Another embodiment of the present invention provides the method according to embodiment [2], wherein the fungal infection is caused by a fungus of the genus *Blastomyces, Candida, Cryptococcus, Epidermophyton, Microsporum, Trichophyton,* or *Pityrosporum.*

[4] Another embodiment of the present invention provides the method according to embodiment [2], wherein the fungus is *Blastomyces dermatidis, Candida albicans, Candida guilliermoundi, Cryptococcus neoformans Microsporum canis, Microsporum audouinii, Microsporum gypseum, Trichophyton tonsuran, Trichophyton rubrum, Trichophyton mentagrophyte, Epidermophyton floccosum, Pityrosporum ovale,* or a combination thereof.

[5] Another embodiment of the present invention provides the method according to any one of embodiments [1]–[4], wherein the mammal is a human.

[6] Another embodiment of the present invention provides the method according to any one of embodiments [1]–[5], wherein the therapeutically effective amount is about 0.1 μg to about 500 mg.

[7] Another embodiment of the present invention provides the method according to embodiment [2], wherein the fungal infection is caused by *Blastomyces dermatidis* or *Cryptococcus neoformans*.

[8] Another embodiment of the present invention provides the method according to embodiment [2], wherein the yeast infection is caused by *Pityrosporum ovale*.

[9] Another embodiment of the present invention provides the method according to any one of embodiments [1]–[8], further comprising administering lupeol either sequentially or simultaneously with a second therapeutic agent.

[10] Another embodiment of the present invention provides the method according to embodiment [9], wherein the second therapeutic agent is at least one of an anti-fungal agent, an anti-yeast agent, an antibiotic agent, or an antiviral agent.

[11] Another embodiment of the present invention provides the method according to any one of embodiments [1]–[10], wherein the therapeutically effective amount of lupeol is administered as a topical formulation.

[12] Another embodiment of the present invention provides a method of inhibiting or killing a fungus or yeast, the method comprising contacting the fungus or yeast with an effective anti-fungal or anti-yeast amount of lupeol.

[13] Another embodiment of the present invention provides the method according to embodiment [12], wherein the fungus is a dermatophytic fungus selected from *Blastomyces, Candida, Cryptococcus, Epidermophyton, Microsporum, Trichophyton,* or *Pityrosporum*.

[14] Another embodiment of the present invention provides the method according to embodiment [12], wherein the dermatophytic fungus is *Blastomyces dermatidis, Candida albicans, Candida guilliermoundi, Cryptococcus neoformans Microsporum canis, Microsporum audouinii, Microsporum gypseum, Trichophyton tonsuran, Trichophyton rubrum, Trichophyton mentagrophyte, Epidermophyton floccosum, Pityrosporum ovale*, or a combination thereof.

[15] Another embodiment of the present invention provides the method according to embodiment [12], wherein the fungus is *Candida albicans* or *Candida guilliermoundi*.

[16] Another embodiment of the present invention provides the method according to embodiment [12], wherein the fungus is *Blastomyces dermatidis* or *Cryptococcus neoformans*.

[17] Another embodiment of the present invention provides the method according to embodiment [12], wherein the yeast is *Pityrosporum ovale*.

[18] Another embodiment of the present invention provides the method according to any one of embodiments [12]–[17], wherein the lupeol is applied using a topical composition.

[19] Another embodiment of the present invention provides the method according to any one of embodiments [12]–[18], further comprising contacting the fungus or yeast either sequentially or simultaneously with a second therapeutic agent.

[20] Another embodiment of the present invention provides the method according to embodiment [19], wherein the second therapeutic agent is at least one of an anti-fungal agent, anti-yeast agent, an antibiotic agent, or an antiviral agent.

[21] Another embodiment of the present invention provides a method for enhancing skin appearance, the method comprising administering to the skin a topical composition with a cosmetically effective amount of lupeol.

[22] Another embodiment of the present invention provides the method according to embodiment [21], wherein the lupeol is present in a concentration of about 0.001 μg/ml to about 5000 μg/ml.

[23] Another embodiment of the present invention provides the method according to embodiment [21], wherein lupeol is present in a concentration of about 12.5 μg/ml to about 1000 μg/ml.

[24] Another embodiment of the present invention provides a pharmaceutical composition comprising a therapeutically effective anti-fungal or anti-yeast amount of lupeol and a carrier.

EXAMPLES

Example 1

Lupeol, Monoglynol B, β-Viscol, Fagarasterol, lup-20(29)-ene-3β-ol

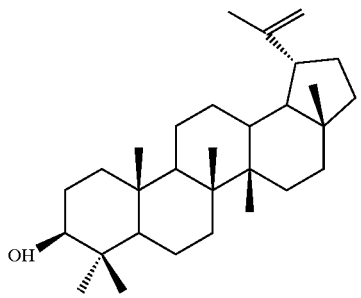

Isolation of Betulin.

Betulin was isolated from paper birch (*B. papyrifera*) bark. Shredded, dry bark (500 g) has been extracted with chloroform on a Soxhlet apparatus for 10 hours. The extract was evaporated and then was left overnight at 5–7° C. Crystals were filtered and washed with hexane and then dried in oven to give 94.5 g of crude Betulin. Double crystallization from chloroform and then mixture of chloroform-isopropyl alcohol (4:1) gives 64–68 g of pure Betulin mp. 258–259° C. [lit. mp 256–261° C.]. IR (KBr) 3378, 2942, 2868, 1645, 1453, 1374, 1106, 1031, 880 cm$^{-1}$; $^1$H NMR (CDCl$_3$) d 4.68 (S, 1H, 29-H), 4.58 (S, 1H, 29-H), 3.8 (D, J=10.3 Hz, 1H, 28-H), 3.34 (D, J=10.3 Hz, 1H, 28-H), 3.18 (DD, 1H, 3-H), 2.38 (M, 1H, 19-H), 1.68 (S, 3H, 30-Me), 0.76, 0.82, 0.97, 0.98, 1.02 (all S, 5×3H, 27-, 23-, 24-, 25-, 26-Me), 1.01–2.4 (complex CH—, CH$_2$, 25H,); $^{13}$C NMR (CDCl$_3$) d 151.249, 110.464, 79.736, 61.278, 56.017, 51.12, 49.48, 48.533, 48.534, 43.454, 41.647, 39.614, 39.432, 38.033, 37.894, 34.958, 34.725, 30.469, 29.901, 28.742, 28.123, 27.773, 25.929, 21.572, 19.845, 19.051, 16.879, 16.726, 16.136, 15.516; MS (EI) 442, 424, 411, 398, 393, 381, 288, 234, 207, 203, 189, 175, 161, 147, 135, 121, 107.

Combined parts after Betulin crystallization and solvent evaporation were separated on silica gel (eluent hex:ether= 10:1). After 150 ml solvent delay 20 fractions were collected. Fractions 1–7 contain mixture of lower terpenes, fractions 8–13 contained Lupeol mp 182.7–187.3° C., IR (KBr) 3380, 2920, 1450, 1405, 1025, 940 cm$^{-1}$; $^1$H NMR (CDCl$_3$) d 4.69 (S, 1H, 29-H), 4.55 (S, 1H, 29-H), 3.18 (DD, 1H, 3-H), 2.35 (M, 1H, 19-H), 1.67 (S, 3H, 30-Me), 0.74, 0.76, 0.80, 0.92, 0.94, 1.01 (all S, 6×3H, 27-, 23-, 24-, 25-, 26-, 28-Me), 1.01–2.4 (comples CH—, CH$_2$, 25H,); $^{13}$C NMR (CDCl$_3$) d 151.32, 109.67, 79.32, 55.63, 50.77, 48.63, 48.33, 43.34, 43.17, 41.16, 40.34, 39.20, 39.04, 38.38, 37.50, 35.92, 34.61, 30.18, 28.33, 27.77, 26.09, 25.47, 21.26, 19.65, 18.65, 18.35, 16.46, 16.31, 15.72, 14.89; MS (EI) 426, 411, 393, 381, 369, 315, 281, 257, 218, 207, 189, 175, 161, 147, 135, 121, 107.

Example 2

In this example, the antifungal properties of lupeol was determined by the direct addition method and the disk diffusion method.

Direct addition method. Sabouraud dextrose agar was prepared according to the manufacturer's instructions and 5.0 ml was dispensed in each 100×25 mm tube. The tubes were autoclaved. To each tube containing 5.0 ml of liquid agar at 45° C., 20 mg of solid test compound was added, to give a final concentration of 4 mg/ml. The agar was solidified in slants. The fungal cultures were then innoculated. The slants were incubated at 25–28° C. for 10–12 days, and the growth of the fungus was recorded every second day. The results in Table 2 indicate growth at the 12th day of inoculation.

Disk diffusion method. Sabouraud dextrose agar was prepared according to the manufacturer's directions, autoclaved, and solidified in sterile petri dishes. Yeast cultures were spread over the surface with a cotton swab. Filter paper disks of 10 mm diameter were each impregnated with one of the test chemicals and then placed on the plate with sterile forceps. The disks were impregnated with 10 μl of a DMSO solution of the test compound at concentrations varying from 1–10 mg/ml. Zones of inhibition were measured after 24 hours.

Results

The results of the assays of growth inhibition by the direct addition method with various strains of fungi are shown in Table 1. The compounds exhibiting the best anti-fungal or anti-yeast activity by the direct addition method were the following:

Using the disk diffusion method, lupeol was not found to inhibit growth of *Pityrosporum ovale* (data not shown). However, by direct addition assays, lupeol inhibited the growth of *P. ovale*. The results of direct addition assays against *P. ovale* are shown in Table 2.

Against *Pityrosporum ovale*, lupeol inhibited the growth by the direct addition method at 4 mg/ml. However, minimum inhibitory concentrations were not determined. The result is comparable to the result with Nystatin, the standard drug against *P. ovale* infection, which also inhibits growth at 4 mg/ml.

TABLE 2

Anti *Pityrosporum ovale* activity of different compounds by direct addition into the *Pityrosporum agar*.

|   | Test Compound | Concentration of compound in the agar | *Pityrosporum ovale* growth |
|---|---|---|---|
| 1. | Lupeol | 4 mg/ml | + |
|   | Control Drugs |   |   |
| 2. | Nystatin | 4 mg/ml | +/− |
| 3. | Griseofulvin | 4 mg/ml | + |
|   | Growth Control |   |   |
| 4. | *P. ovale* Growth Control | No Compound | ++ |

*Pityrosporum ovale* growth measured 18 hours after inoculation
+++ = Maximum Growth
++ = Moderate Growth
+ = Minimum Growth
+/− = Very Little Growth
− = No Growth Example 3

In this example, derivatives of lupeol were tested for their activity in inhibiting the growth of *Trichophyton mentagraphytes* in liquid culture.

Direct addition to liquid culture method. Sabouraud dextrose broth was prepared according to the manufacturer's instructions, and 7.0 ml was dispensed into 100×25 mm tubes and autoclaved. To each tube containing 7.0 ml of liquid broth, the test compounds dissolved in DMSO were added to final concentrations of 25, 50, and 100 μg/ml. The tubes were then inoculated with 150 μl of a fungus suspension and incubated at 25–28° C. for 10–12 days. Growth was measured every second day by measuring optical density at 600 nm against a blank containing sterile broth.

Results.

The optical density of the cultures of *Trichophyton mentagrophytes* after 12 days of growth in broth with various concentrations of the test compounds is shown in FIG. 1. The full names of the compounds listed in the figure are as follows. "Maleate" refers to lupeol-3-maleate. "Diketone" refers to lupenon-1,2-ene-2-ol. "Dimethylsuccinate" refers to lupeol-3-(3',3'-dimethyl)succinate. "Amine" refers to lupeol-3-amine.

Lupeol and all of its derivatives that were tested inhibited the growth of the fungus. The degree of inhibition with 100 μg/ml of the test compounds was comparable to the extent of inhibition with 50 or 100 μg/ml of Nystatin or Lamisil, two standard anti-fungal compounds.

TABLE 1

Antifungal activities of lupeol against human pathogenic fungi.

| Test Antifungal Compounds | Concentration mg/mL of agar | *Microsporum canis* | *Epidermophyton floccosum* | *Microsporum audouinni* | *Trichophyton rubrum* | *Pityrosporum ovale* | *Microsporum gypseum* | *Trichophyton tonsuran* | *Trichophyton mentagrophytes* |
|---|---|---|---|---|---|---|---|---|---|
| Lupeol | 4 mg | + | − | + | + | − | NP | NP | NP |
| Control | − | ++ | − | ++ | + | − | +++ | +++ | +++ |

Fungal growth at the 12th day after inoculation
+++ = Maximum Fungal Growth
++ = Moderate Fungal Growth
+ = Minimum Fungal Growth
+/− = Very Little Fungal Growth
− = No Fungal Growth
NP = Assay not performed

Example 4

This example summarizes the results of various other assays of the anti-fungal activity of lupeol. The results are shown in Table 3. Table 3 summarizes results using different assay methods—direct addition, agar dilution, and direct addition to liquid culture, as disclosed in the previous Examples 2 and 3.

TABLE 3

Activity of lupeol against human pathogenic fungi and yeasts.

| S. No. Compound | Candida albicans | Candida guilliermoundi | P. ovale | Blastomyces dermatidis | Crytococcus neoformans | Microsporum canis | Microsporum audouinii | Microsporum gypseum | Trichophyton tonsuran | Trichophyton rubrum | Trichophyton mentagrophytes | Epidermophyton floccosum |
|---|---|---|---|---|---|---|---|---|---|---|---|---|
| Lupeol | x | x | x | | | x | x | x | x | x | x | x |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating a fungal infection or a yeast infection in a mammal, the method comprising administering to the mammal in need of such treatment or at risk thereof a therapeutically effective amount of lupeol,

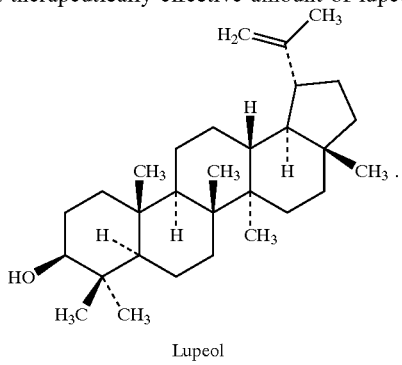

Lupeol

2. The method according to claim 1, wherein the fungal infection or yeast infection is caused by at least one dermatophytic fungus.

3. The method according to claim 2, wherein the fungal infection is caused by a fungus of the genus *Blastomyces, Candida, Cryptococcus, Epidermophyton, Microsporum, Trichophyton,* or *Pityrosporum.*

4. The method according to claim 2, wherein the fungus is *Blastomyces dermatidis, Candida albicans, Candida guilliermoundi, Cryptococcus neoformans Microsporum canis, Microsporum audouinii, Microsporum gypseum, Trichophyton tonsuran, Trichophyton rubrum, Trichophyton mentagrophyte, Epidermophyton floccosum, Pityrosporum ovale,* or a combination thereof.

5. The method according to claim 1, wherein the mammal is a human.

6. The method according to claim 1, wherein the therapeutically effective amount is about 0.1 μg to about 500 mg.

7. The method according to claim 2, wherein the fungal infection is caused by *Blastomyces dermatidis* or *Cryptococcus neoformans.*

8. The method according to claim 2, wherein the yeast infection is caused by *Pityrosporum ovale.*

9. The method according to claim 1, further comprising administering lupeol either sequentially or simultaneously with a second therapeutic agent.

10. The method according to claim 9, wherein the second therapeutic agent is at least one of an antifungal agent, an anti-yeast agent, an antibiotic agent, or an antiviral agent.

11. The method according to claim 1, wherein the therapeutically effective amount of lupeol is administered as a topical formulation.

12. A method of inhibiting or killing a fungus or yeast in mammalian tissue, the method comprising contacting the fungus or yeast in mammalian tissue with an effective anti-fungal or anti-yeast amount of lupeol.

13. The method according to claim 12, wherein the fungus is a dermatophytic fungus selected from *Blastomyces, Candida, Cryptococcus, Epidermophyton, Microsporum, Trichophyton,* or *Pityrosporum.*

14. The method according to claim 13, wherein the dermatophytic fungus is *Blastomyces dermatidis, Candida albicans, Candida guilliermoundi, Cryptococcus neoformans Microsporum canis, Microsporum audouinii, Microsporum gypseum, Trichophyton tonsuran, Trichophyton rubrum, Trichophyton mentagrophyte, Epidermophyton floccosum, Pityrosporum ovale,* or a combination thereof.

15. The method according to claim 12, wherein the fungus is *Candida albicans* or *Candida guilliermoundi.*

16. A method of inhibiting or killing a fungus, the method comprising contacting the fungus with an effective anti-fungal amount of lupeol, wherein the fungus is *Blastomyces dermatidis* or *Cryptococcus neoformans.*

17. A method of inhibiting or killing a yeast, the method comprising contacting the yeast with an effective anti-yeast amount of lupeol, wherein the yeast is *Pityrosporum ovale.*

18. The method according to claim 11, further comprising contacting the fungus or yeast either sequentially or simultaneously with a second therapeutic agent.

19. The method according to claim 18, wherein the second therapeutic agent is at least one of an anti-fungal agent, anti-yeast agent, an antibiotic agent, or an antiviral agent.

20. A method for enhancing the appearance of skin or nail that is infected with a fungus or yeast, the method comprising administering to the infected skin or nail a topical composition that comprises a pharmaceutically or cosmetically suitable carrier and a cosmetically effective amount of lupeol.

21. The method according to claim 20, wherein the lupeol is present in a concentration of about 0.001 μg/ml to about 5000 μg/ml.

22. The method according to claim 20, wherein lupeol is present in a concentration of about 12.5 μg/ml to about 1000 μg/ml.

23. The method according to claim 20, wherein lupeol is present in a concentration of up to about 10 wt. %.

24. A method for enhancing the appearance of skin or nail that is infected with a fungus or yeast, the method comprising administering to the infected skin or nail a topical composition that comprises a pharmaceutically or cosmetically suitable carrier and at least about 1 μM lupeol.

* * * * *

UNITED STATES PATENT AND TRADEMARK OFFICE
CERTIFICATE OF CORRECTION

PATENT NO. : 6,951,847 B2 Page 1 of 1
APPLICATION NO. : 10/431351
DATED : October 4, 2005
INVENTOR(S) : Gibson et al.

It is certified that error appears in the above-identified patent and that said Letters Patent is hereby corrected as shown below:

In column 2, line 16, after "organisms" delete "wih" and insert -- with --, therefor.

In column 3, line 52, delete "nontoxic" and insert -- non-toxic --, therefor.

In column 8, line 66, delete "comples" and insert -- complex --, therefor.

In column 12, line 2, in Claim 10, delete "antifungal" and insert -- anti-fungal --, therefor.

Signed and Sealed this

Third Day of April, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,951,847 B2 |
| APPLICATION NO. | : 10/431351 |
| DATED | : October 4, 2005 |
| INVENTOR(S) | : Gibson et al. |

It is certified that error appears in the above-identified patent and that said Letters Patent is hereby corrected as shown below:

On the title page item (75) Inventor: after "David J. Gibson, Woodbury, NJ (US); Robert M. Carlson, Duluth, MN (US)", insert -- M. Reza-ul Karim, Duluth, MN (US) --.

Signed and Sealed this

Seventh Day of April, 2009

JOHN DOLL
*Acting Director of the United States Patent and Trademark Office*